(12) United States Patent
Freidhof et al.

(10) Patent No.: US 9,709,610 B2
(45) Date of Patent: Jul. 18, 2017

(54) SYSTEM COMPRISING A PROBE AND A MEASURING DEVICE

(71) Applicant: Rohde & Schwarz GmbH & Co. KG, Munich (DE)

(72) Inventors: Markus Freidhof, Kirchseeon (DE); Martin Peschke, Munich (DE)

(73) Assignee: Rohde & Schwarz GmbH & Co. KG, Munich (DE)

( * ) Notice: Subject to any disclaimer, the term of this patent is extended or adjusted under 35 U.S.C. 154(b) by 64 days.

(21) Appl. No.: 14/634,508

(22) Filed: Feb. 27, 2015

(65) Prior Publication Data
US 2015/0247885 A1  Sep. 3, 2015

(30) Foreign Application Priority Data
Feb. 28, 2014 (DE) .................. 10 2014 203 730

(51) Int. Cl.
| | |
|---|---|
| *G01R 1/067* | (2006.01) |
| *G01R 19/22* | (2006.01) |
| *G01R 19/12* | (2006.01) |
| *G01N 1/00* | (2006.01) |
| *G01R 1/00* | (2006.01) |
| *G01R 21/06* | (2006.01) |

(52) U.S. Cl.
CPC ......... *G01R 19/22* (2013.01); *G01R 1/06766* (2013.01); *G01R 1/06777* (2013.01); *G01R 19/12* (2013.01); *G01N 1/00* (2013.01); *G01N 2201/00* (2013.01); *G01R 1/00* (2013.01); *G01R 21/06* (2013.01)

(58) Field of Classification Search
CPC .............................. G01R 1/00; G01N 2201/00
See application file for complete search history.

(56) References Cited

U.S. PATENT DOCUMENTS

| | | | | |
|---|---|---|---|---|
| 5,546,082 A | * | 8/1996 | LaRocca | H03M 1/0872 341/128 |
| 2006/0269186 A1 | | 11/2006 | Frame et al. | |
| 2010/0277190 A1 | * | 11/2010 | Reichel | G01R 1/06788 324/754.11 |
| 2010/0305465 A1 | * | 12/2010 | Ricks | A61B 5/0878 600/538 |
| 2012/0119726 A1 | * | 5/2012 | Kuhwald | G01R 13/0254 324/149 |

(Continued)

FOREIGN PATENT DOCUMENTS

| | | |
|---|---|---|
| DE | 102008009962 | 6/2009 |
| DE | 102010033991 | 7/2011 |

*Primary Examiner* — Jermele M Hollington
*Assistant Examiner* — Temilade Rhodes-Vivour
(74) *Attorney, Agent, or Firm* — Lee & Hayes, PLLC (57) ABSTRACT

The invention relates to a system comprising a probe and a measuring device, wherein the probe is connected to an input of the measuring device, and wherein an analog-digital converter is connected downstream of the input of the measuring device. The probe provides an analog-digital converter for the generation of a value-discrete and/or time-discrete signal from an analog input signal, wherein the value-discrete and/or time-discrete signal is supplied to the analog-digital converter of the measuring device. The invention further relates to a method for the registration of an analog signal by means of a system comprising a probe and a measuring device.

17 Claims, 4 Drawing Sheets

(56) References Cited

U.S. PATENT DOCUMENTS

2013/0002284 A1\* 1/2013 Deutinger .............. G01R 21/04
　　　　　　　　　　　　　　　　　　　　324/755.01
2013/0141077 A1\* 6/2013 Wellenstein ......... G01R 15/148
　　　　　　　　　　　　　　　　　　　　324/76.39

\* cited by examiner

SYSTEM COMPRISING A PROBE AND A MEASURING DEVICE

PRIORITY

This application claims priority of German patent application DE 10 2014 203 730.1 filed on Feb. 28, 2014.

FIELD OF THE INVENTION

The invention relates to a system and a method comprising a probe and a measuring device.

BACKGROUND OF THE INVENTION

Conventional active-oscilloscope probes typically provide an analog input for the registration of an analog signal. These probes further comprise an analog output for the output of the analog signal to a measuring device. An active circuit which processes the analog signal registered by means of a probe tip is included in the probe.

A large number of different physical measurement parameters can be registered by means of a probe. In view of this large number, it is necessary to use special probes for the different properties of the measurement parameter to be registered. For example, a different probe must be used for registering a high power signal than for registering a high-frequency signal.

In particular, the output signal provided by the probe is an analog electrical voltage which is processed by a measuring device connected to the probe. In the following, an analog signal is understood to be a time-continuous and value-continuous signal which, for example, provides an infinite and arbitrarily fine signal characteristic and can theoretically assume infinitely many values in the dynamic range. A digitization and recording of the analog signal to be registered is then implemented in the downstream measuring device, especially a digital storage oscilloscope or voltmeter. A specified trigger event is determined for the display of the signal. For the digitization of the signal, an analog-digital conversion is implemented in the measuring device. The signal is optionally conditioned through further analog circuits in the measuring device, for example, input amplified or decoupled. In particular, the measuring device offers extensive functions for triggering, recording, processing and display of the measurement signal to be registered.

It is disadvantageous in an arrangement of this kind that the accuracy of the probe is always limited by the accuracy of the measuring device. A probe which provides substantially better properties, for example, with regard to DC voltage component, accuracy, dynamic range or noise behaviour, is restricted by correspondingly poorer properties of the measuring device, so that the registered signal is impaired in an undesirable manner.

Alongside this, there also exist active probes with digital outputs in which a triggering, recording and processing of the analog input signal takes place in the probe itself. These recorded and digitised data are transmitted asynchronously via a digital interface to the measuring device for display. Such probes require a trigger signal from the measuring device in order to establish a time reference between the registered analog signal and the digitised signal to be transmitted. This trigger signal is specified by the measuring device and must be supplied to the probe via an external trigger-signal line from the measuring device. The provision of the trigger signal for the probe is effort-intensive and undesirable.

Furthermore, it is problematic in this context if measurements of several probes are to be processed in the measuring device in a synchronised manner. Different cable lengths and a poor accuracy of synchronisation lead to considerable measurement errors in the measuring device. Furthermore, the probe is very severely limited in its possibility for recording and processing the measurement data to be registered because of a small probe housing and its low maximum power consumption.

US 2006/026 9186 A1 proposes a probe for high-precision measurements which is connected to an oscilloscope. In this context, a digitization is provided in the probe in order to implement a setting and adjustment of the probe.

One object of the present invention is to provide a system and a method which registers analog measurement signals with high sensitivity and low storage requirement by means of a probe and communicates them to a measuring device. In particular, triggering and synchronisation of the signal to be registered should be provided in a simplified manner.

SUMMARY OF THE INVENTION

According to one aspect of the invention a system comprise a probe and a measuring device. In this context, the probe is connected to an input of the measuring device. An analog-digital converter is connected downstream to the input of the measuring device. The probe provides a converter for the generation of a value-discrete and/or time-discrete signal from the analog input signal. The value-discrete and/or time-discrete signal is supplied to the analog-digital converter of the measuring device.

The probe is preferably embodied with an analog-digital converter and provides a sampled signal to the measuring device. The measuring device now already receives a time-discrete and/or value-discrete signal of the probe. Accordingly, in an advantageous manner, the properties of the measuring device, especially the noise, the dynamic range or the accuracy with regard to the registration of the data are irrelevant, and a measuring device with such relatively poorer properties by comparison with the probe has no influence on the measurement signal to be registered.

By preference, a probe with high resolution can now be connected to a conventional measuring-device input with correspondingly lower resolution without restricting its measurement accuracy. The measurement input of this measuring device receives a continuous digital output datastream from the probe.

As soon as the time-discrete and/or value-discrete signal of the probe is provided to the measuring device, it can be further processed with all of the available functions of the measuring device. In particular, a digital triggering, a digital filtering and further conditioning options through the measuring device are therefore possible.

By preference, the converter of the probe provides a relatively higher resolution than the analog-digital converter of the measuring device. Accordingly, the sensitivity of the probe is not already per se hindered by the relatively lower resolution of the measuring device. The accuracy of the probe can therefore be further utilised for the processing of the measurement signal in the measuring device. In this manner, a probe can be connected both to a very high-quality measuring device and also to a low-quality measuring device, wherein the actual data-processing and data evaluation takes place in the respective measuring device.

In a preferred embodiment, the probe provides a first probe input and a second probe input, wherein each of the probe inputs registers the same measurement parameter.

With a probe of this kind, differential current signals and/or voltage signals can be registered. For this purpose, the probe provides a differential amplifier, wherein only the differential signal which is present between the first and second probe input are processed in the probe as the measurement signal to form a value-discrete and/or time-discrete signal.

In a preferred embodiment, the probe provides a first probe input and a second probe input, wherein each of the probe inputs registers different measurement parameters. Accordingly, for example, a signal to be registered can already be calculated from these two different measurement values in a calculation unit of the probe. The calculated signal is then provided as a time-discrete and/or value-discrete signal to the measuring device. For example, a power measurement is made possible by means of this probe, if a voltage signal is registered by means of the first probe and the current signal is registered by means of the second probe input.

In a preferred embodiment, the probe provides at least one second analog-digital converter for the generation of a second value-discrete and/or time-discrete signal from the analog input signal. In this context, the second value-discrete and/or time-discrete signal is supplied to a second analog-digital converter of the measuring device, wherein, in particular, a second input of the measuring device is used for this purpose.

Accordingly, a probe with several channels can be connected to a measuring device, wherein each of the inputs transmits a time-discrete and value-discrete signal to the measuring device. The calculation and analysis of the supplied signals is then implemented in the measuring device. For example, in this context, the same measurement parameter can be registered in order to control a multi-channel multimeter. In an advantageous manner, this then means that the registered and transmitted measurement signals are displayed in a defined time relationship relative to other channels of the measuring device, wherein an external trigger-signal line from the probe to the measuring device is not required. The complexity of the connection between the probe and the measuring device is then considerably reduced. A simplified triggering and synchronisation is then achieved through the digitization within the probe. In this manner, signals can be registered in a time-synchronous manner with several probes or several channels of a probe. The full digital functions of the measuring device are available for every channel.

In particular, a ground-referenced voltage, a ground-referenced current, a differential voltage, a differential current, an electrical power, a temperature, an optical radiation power, an acoustic sound pressure etc. are conceivable as measurement parameters.

In a preferred embodiment, a value-continuous, time-discrete signal is supplied to the analog-digital converter of the measuring device. Such signals are also designated as sample-and-hold signals.

In a preferred embodiment, value-discrete and time-continuous signals are supplied to the measuring device. In another preferred embodiment, the signal supplied to the analog-digital converter of the measuring device is an OFDM signal or a pulse-width modulated signal.

By preference, the supplied value-discrete and/or time-discrete signal comprises additional parameter information of the probe alongside the registered signal characteristics. Such parameter information includes in particular an identification number of the probe or calibration information in order to compensate parasitic effects of the probe. Such parameter information is evaluated by the measuring device and then used for the automatic adjustment and calibration of the probe.

The system according to one aspect of the invention provides a probe which requires no trigger signal of the measuring device since a time-discrete and/or value-discrete signal is transmitted as a continuous datastream to the measuring device. The time reference with regard to the supplied value-discrete and/or time-discrete signal is preserved, because every sampled value of the probe is transmitted to the measuring device in a fixed time reference. The time reference between registered analog signal and transmitted time-discrete and/or value-discrete signal is accordingly provided at all times. Accordingly, a separate trigger-signal line between probe and measuring device can be dispensed with. The triggering of the measurement signal for display purposes and synchronisation purposes takes place in the measuring device.

In a preferred embodiment, a marking of a sampled value at which the triggering is to take place is provided by the probe itself. The marking takes place, for example, through a trigger bit in a continuous datastream of the time-discrete and/or value-discrete signal. Accordingly, a trigger time is specified by the probe and supplied to the measuring device within the framework of the time-discrete and/or value-discrete signal. In this context, the marking indicates only which sample value is to be used as the trigger time. An external trigger-signal line is therefore not required. With this system, a high precision in the registering of the measurement signal by the probe is ensured, wherein the selection of the sampled values of the analog signal provided by the probe is implemented by the measuring device itself. Accordingly, high-quality probes can be used both for high-precision measuring devices and also for conventional measuring devices, without showing loss of sensitivity resulting from a poor measuring device.

A storage of the time-discrete and/or value-discrete signals within the probe is not necessary, since the signals are connected to a digital input of the measuring device. The value-discrete signals to the measuring device can be binary, ternary, or quaternary etc., or can have another arbitrary level within a value-discrete transmission method.

According to the invention, a method is provided for the registration of an analog signal by means of a system comprising a probe and a measuring device. The method comprises the method steps: registration of the analog signal by means of the probe; conversion of the registered analog signal into a value-discrete and/or time-discrete signal by means of the probe; supply of the converted value-discrete and/or time-discrete signal to the measuring device and conversion of the value-discrete and/or time-discrete signal into a digital signal by the measuring device for further processing in the measuring device.

BRIEF DESCRIPTION OF THE DRAWINGS

In the following, exemplary embodiments of the invention are explained in greater detail with reference to the Figures of the drawings by one way of example only. In this context, identical components are shown with identical reference numbers. Individual components in the drawings may have been illustrated with exaggerated scale or exaggerated simplification. The drawings show:

FIG. 2b a time-discrete signal generated according to the invention and supplied to the measuring device based on the analog signal shown in FIG. 2a;

FIG. 7b a sampling function for the sampling of the signal shown in FIG. 7a.

DETAILED DESCRIPTION OF THE DRAWINGS

Figure 1:
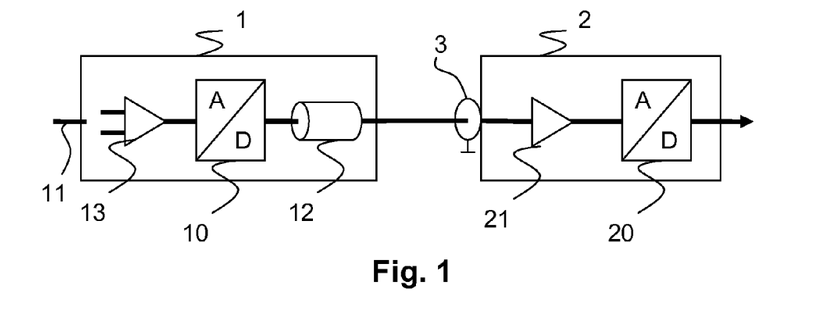
FIG. 1 a block-circuit diagram of a first exemplary embodiment of the system according to the invention.
Figure 2A:
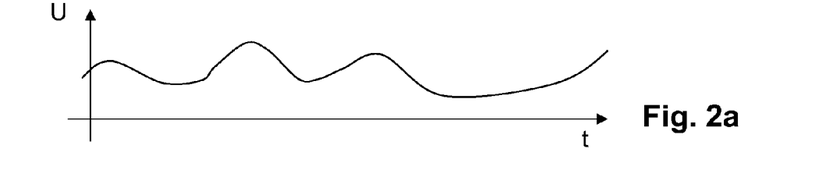
FIG. 2a an analog measurement signal to be registered.

FIG. 1 shows a block-circuit diagram of a system according to the invention comprising a probe 1 and a measuring device 2. In particular, the measuring device 2 is a digital storage oscilloscope. Alternatively, the measuring device 2 is a voltmeter or a signal analyser. The probe 1 provides a probe input 11, also designated as a probe tip. An analog input signal, as shown by way of example in FIG. 2a, is connected to the probe input 11. The analog input signal is optionally amplified by means of an amplifier 13 within the probe 1. Following this, an analog-digital conversion of the analog input signal is implemented by means of an analog-digital converter 10 of the probe 1. The output of the analog-digital converter 10 makes available a value-discrete and time-discrete signal, which is supplied to a measuring device by means of a measurement line 12 at the input 3 of the measuring device 2. However, a signal which is only value-discrete or only time-discrete can also be used.

The measuring device 2 optionally comprises a conditioning unit 21, which conditions the time-discrete and/or value-discrete signal of the probe 1 for an analog-digital converter 20 of the measuring device 2. A digitised signal which is available for further processing within the measuring device 2 is present at the output of the analog-digital converter 20 of the measuring device 2. In particular, a display of the signal and a further evaluation of the signal are provided. For example, a digital filter and/or a digital trigger unit can be connected downstream within the measuring device 2.

By way of difference from an analog probe according to the prior art, the input 3 of the measuring device 2 takes over the reception of the digital output data from the probe 1. The properties of the measuring device 2 with regard to noise, dynamic range or accuracy are therefore completely irrelevant to the registration of the measurement signal. For example, a probe 1 with a high resolution, for example, 16-bits with one Mega-sample per second, can be connected without restricting its measurement accuracy to the measurement-signal input 3 of the measurement signal 2 with relatively lower resolution, for example, only 8 bits, but 10 Giga-samples per second.

The input 3 of the measuring device 2 receives a continuous output datastream of the probe 1 which provides a signal rate of 16 Mega-bits per second in the example named here. As soon as this datastream is present in the measuring device 2, this supplied value-discrete and/or time-discrete signal can be further processed. In particular, a digital triggering for the display, a synchronisation with further channels of the measuring device 2 and/or a digital filtering of the signal are provided. Frequency analyses can be implemented in a similar manner.

FIG. 2a shows an analog input signal to be registered. The input signal in FIG. 2a is a time-continuous and value-continuous voltage signal which is plotted against time. This input signal is registered by means of the probe tip 11 of the probe 1. In a preferred embodiment, an amplifier 13 is connected downstream of the probe tip 11 in order to convert the signal into a dynamic range optimal for the analog-digital converter 10. In this context, the amplifier 13 is provided optionally for the probe 1.

Figure 2B:
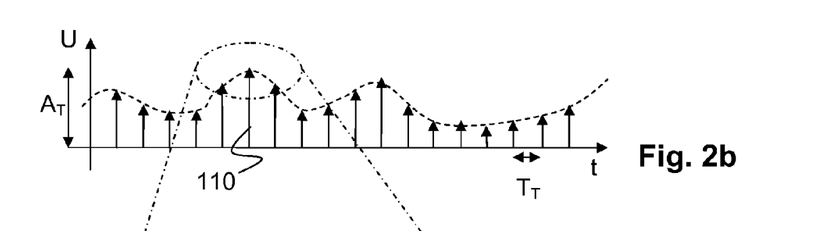

FIG. 2b shows that the value-continuous and time-continuous input signal is converted into a value-discrete and time-discrete signal by means of the analog-digital converter 10. In this context, in order to fulfil the sampling theorem, the sampling period $T_T$ of the analog-digital converter 10 of the probe 1 is at least twice as short as the oscillation duration of the maximum frequency disposed within the analog input signal according to FIG. 2a.

Figure 2C:
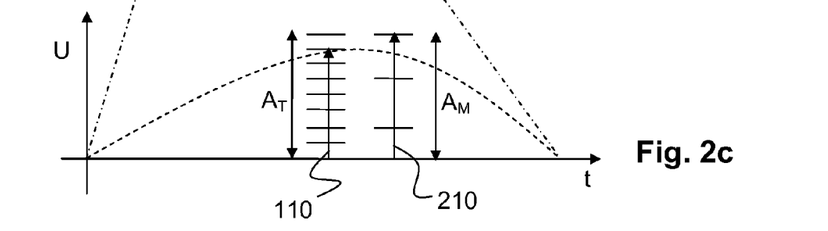
FIG. 2c a sub-region of the measurement signal according to the invention shown in FIG. 2b.

On the basis of the sampled value 110 from FIG. 2b, according to FIG. 2c, the different resolution $A_T$ of the probe 1 is illustrated by comparison with the resolution $A_M$ of the measuring device 2. For this purpose, the difference between a sampled value 110 of the analog-digital converter 10 of the probe 1 and the sampled value 210 of the analog-digital converter 20 of the measuring device 2 is illustrated in FIG. 2c. The sampled value 110 corresponds to the sampled value 210, so that both sampled values 110, 210 should represent an identical point in the analog input signal.

It is evident that the resolution $A_T$ of the probe 1 is substantially higher, so that a very much more precise approximation of the sampled value 110 to the actual level of the input signal is reached. In FIG. 2c, a resolution $A_T$ of the probe 1 of eight levels is provided in this region of the signal. By contrast, the sampled value 210 of the measuring device 2 shows a much higher voltage value. Since the sampled value 210 provides only 3-levels because of the resolution $A_M$ of the measuring device 2, a falsification of the input signal by a relatively large error value would occur if the measuring device 2 were to perform the analog-digital conversion. According to the invention, the supply of the measurement signal takes place with a time-discrete and/or value-discrete signal. The accuracy of the sampling is therefore not lost as a result of the relatively higher resolution. The value-discrete and/or time-discrete signals can be taken over from the probe. In this manner, a measurement signal which provides a high dynamic range, a relatively low noise and a high precision can be received and evaluated.

FIG. 1 and FIG. 2 show that the use of a system according to the invention comprising a probe 1 and measuring device 2 ensures that the noise, dynamic range and accuracy of the measuring device 2 are completely irrelevant to the registration of the signal. Accordingly, high-quality and maximum quality signals are consistently provided at the input 3 of the measuring device 2. The signals can be directly further processed because of their value-discrete and/or time-discrete embodiment.

In the system according to the invention, no trigger line is provided between the probe 1 and measuring device 2. This is possible because the probe 1 provides a continuous datastream in a digital form (time-discrete and/or value-discrete), and the time reference is therefore preserved at all times. With a system according to the invention of this kind, the basic accuracy during the registration of the signal is increased.

Figure 3:
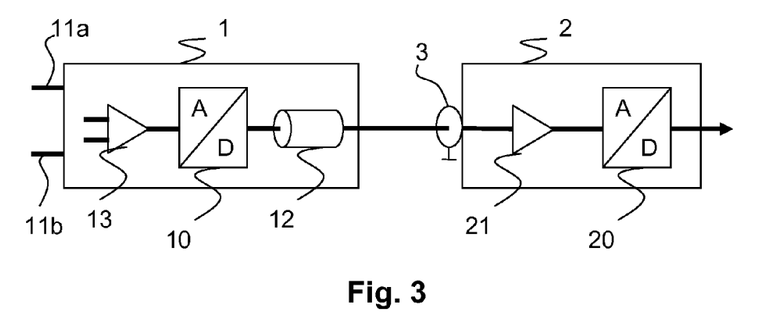
FIG. 3 an alternative exemplary embodiment to FIG. 1 of a system according to the invention.

FIG. 3 shows an alternative exemplary embodiment to FIG. 1 of a system according to the invention. The only difference by comparison with FIG. 1 is that the probe 1 provides a first probe input 11a and a second probe input 11b. The amplifier 13 in a scenario of this kind is a differential amplifier. Differential signals can be registered by means of this set up. Only the potential difference between the first probe input 11a and the second probe input 11b is registered and amplified.

Figure 4:
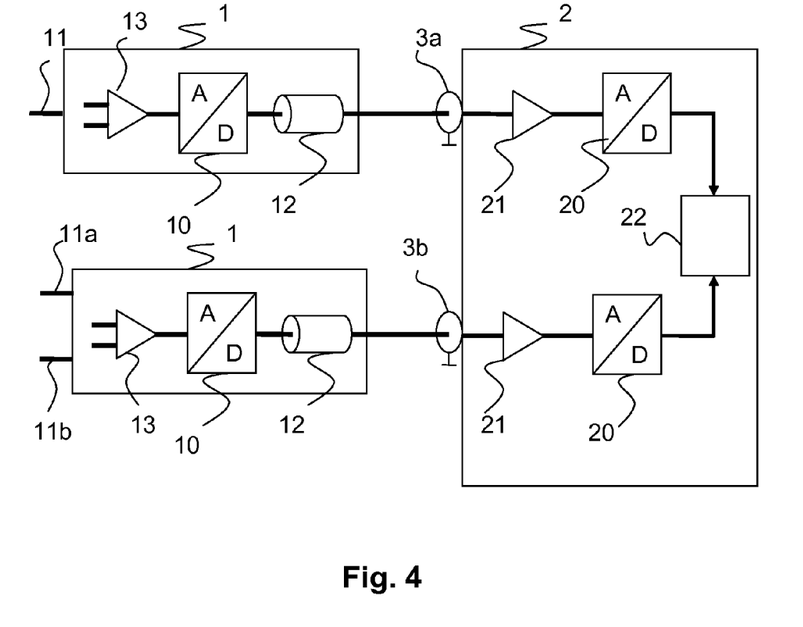
FIG. 4 an alternative system according to the invention to FIGS. 1 and 3.

FIG. 4 shows an alternative exemplary embodiment to FIG. 1 and FIG. 3 of a system according to the invention. By way of difference from the systems shown in FIG. 1 and FIG. 3, the measuring device 2 provides a first measurement input 3a and a second measurement input 3b. Probes 1 are connected to each of the measurement inputs 3a, 3b. In FIG. 4, a first probe 1, which provides only one probe input 11 and corresponds to the probe 1 in FIG. 1, is connected to the input 3a. By contrast, a probe 1 which provides two probe inputs 11a, 11b and corresponds to the probe 1 of FIG. 3, is connected to the measurement input 3b of the measuring device 2.

The probes 1 can register the same measurement parameters. Accordingly, for example, a voltage difference between different points of a circuit arrangement can be registered by means of the probes, wherein, in each case, one time-discrete and/or value-discrete signal per probe 1 is supplied to the measuring device 2 via the measurement inputs 3a, 3b. The measuring device 2 displays the supplied probe signals, wherein a time synchronisation is implemented by the measuring device 2. Furthermore, calculations with the supplied signals can be implemented by means of a calculation unit 22.

With the use of the set up according to FIG. 4 for the same measurement parameters, for example, a voltage, intermediate values can be determined in the calculation unit 22, for example, by addition or subtraction. In particular, the calculation unit takes over a synchronisation of the continuous datastreams provided from the probes 1. In this manner, a synchronisation and triggering by means of an external signal, for example, a signal line between probe and measuring device 2 can be saved.

Alternatively, with the use of the set up according to FIG. 4 for different measurement parameters, for example, voltage and current, intermediate values can be calculated in the calculation unit 22 by multiplication or division. Further calculations, especially, a frequency analysis of the signals are also conceivable.

Figure 5:
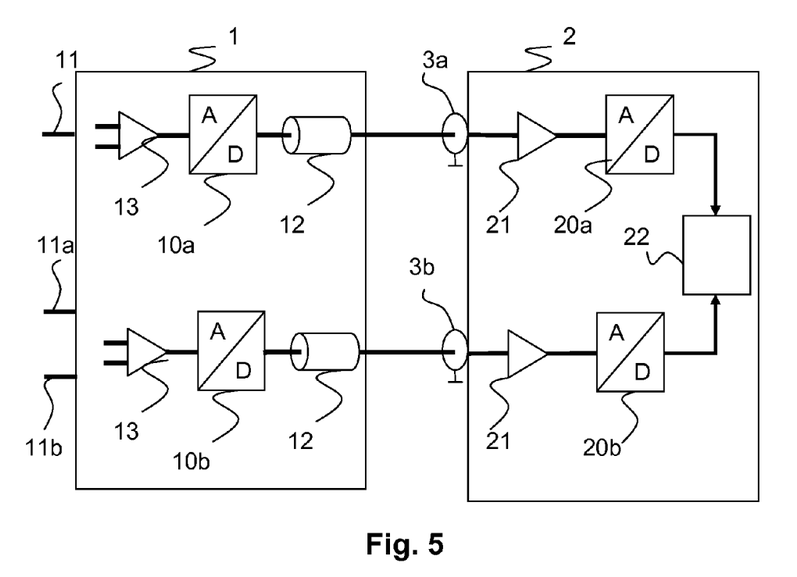
FIG. 5 an alternative system according to the invention to FIGS. 1, 3 and 4.

FIG. 5 shows an alternative exemplary embodiment to FIG. 1, 3 or 4 of the system according to the invention. By way of difference from FIG. 4, only one probe 1 is provided, which comprises a plurality of inputs 11, 11a, 11b. Furthermore, the probe 1 comprises a plurality of analog-digital converters 10a, 10b and makes available at different measurement inputs 3a, 3b of the measuring device 2 a plurality of time-discrete and/or value-discrete signals. In this context, the synchronisation and also triggering of the signals is implemented via a calculation unit 22 of the measuring device 2.

With the method according to the invention, a large number of new probes 1 are conceivable for the measuring devices 2. For example, a probe 1 with a substantially higher resolution, especially 12 bits, 16 bits, 24 bits, can be connected to a measuring device, wherein the measuring device 2 can process the generated datastream of a time-discrete and/or value-discrete signal further in this high resolution. The probes 1 can be used for a variety of different applications. Since neither synchronisation nor triggering need to be implemented, the connection between probe 1 and measuring device 2 is embodied in a simplified manner.

In particular, a probe 1 with several channels can be used in order to register the same measurement parameter, voltage or current etc. For example, a four-channel multimeter can be configured with it.

For instance, probes with channels which register different measurement parameters can also be used. For example, voltage and current can be multiplied in order to determine a power. Common-mode voltages can be subjected to a differential measurement. The complexity of the system according to the invention is limited only by the maximum reception speed of the measurement input 3 of the measuring device 2.

Figure 6A:
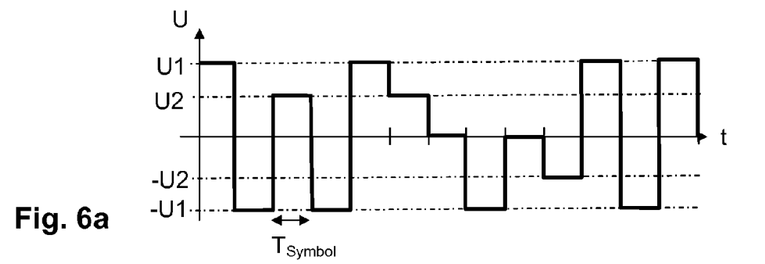
FIG. 6a an alternative value-discrete and time-continuous signal according to the invention to FIG. 2b supplied to the measuring device.

Because of the relatively higher-quality reception-measurement accuracy, even finely-stepped value-discrete signals can now be transmitted, registered and evaluated. In particular, FIG. 6a shows a value-discrete, time-continuous signal which is supplied to the measuring device 2. These signals are also designated as sample-and-hold signals. According to FIG. 6a, a symbol duration $T_{Symbol}$ is constant, whereas the value of the voltage varies between the values U1, U2, −U1 and −U2. The number of voltage steps in this context is not restricted. In this context, a higher-quality transmission method is no longer necessary, since the probe 1 already provides a high resolution $A_T$ for the registration of the individual voltage levels.

Figure 6B:
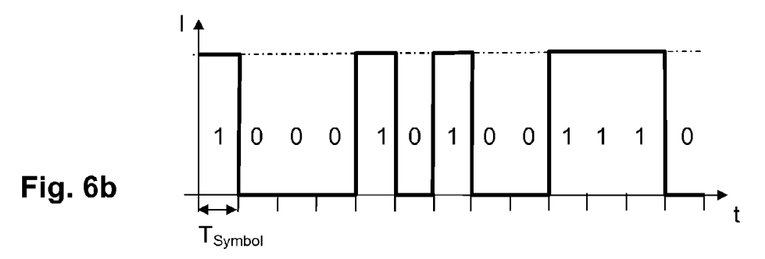
FIG. 6b an alternative value-discrete and time-continuous signal according to the invention to FIGS. 2b and 6a supplied to the measuring device.

FIG. 6b shows an alternative value-discrete, time-continuous signal, which is supplied to the measuring device 2. This signal is a pulse-width modulated signal. The accuracy of the system according to the invention is significantly influenced by the probe 1 and serves to increase the accuracy of the system as a whole.

Figure 7A:
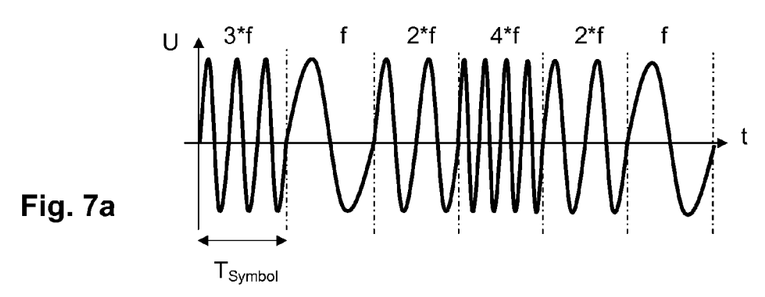
FIG. 7a an FSK-signal as an input signal to be registered.
Figure 7B:
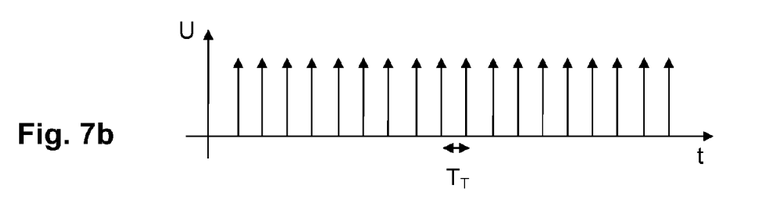

FIG. 7a shows an analog input signal. The input signal is a strongly simplified signal within a frequency-shift-keying method, abbreviated as FSK. In this context, signals with the basic frequency f, double the basic frequency $2f$, three times the basic frequency $3f$ and four times the basic frequency $4f$ are transmitted as a digital symbol within one symbol duration $T_{Symbol}$. Registering such signals requires a high precision. These signals are registered by means of the analog-digital converter 10 of the probe 1 with a high precision.

One preferred embodiment additionally provides for the continuous datastream supplied from the probe 1 to transmit parameter information about the probe 1 itself. For this purpose, the probe 1 provides a store with parameter information disposed within it, in particular, an identification number ID or calibration information.

This is possible, for example, within the framework of a protocol data transmission, so that, alongside the payload data, protocol data with the parameter information are also transmitted periodically, or alternatively, at the time of the first connection of the probe 1 to the measuring device 1. Alternatively, the parameter information is transmitted with a certain time interval, for example, every 10 ms, at the time of plugging the probe 1 into the measuring device 2. Alternatively, the parameter information is transmitted once at the plug-in time for a given duration, for example, two seconds. The parameter information contains, in particular, information about the size of parasitic elements, especially of an equivalent series resistor or equivalent parallel resistor, an equivalent series capacitor or equivalent parallel capacitor and/or an equivalent series inductance or equivalent parallel inductance. These properties of the probe and are used to implement an automatic adjustment and calibration of the probe 1 by the measuring device 2, in order to prevent measurement inaccuracies based on error matching between the probe 1 and the measuring device 2.

In a preferred embodiment, the measuring device is a logic analyser. In this case, a comparator which conditions a time-continuous but value-discrete signal and makes it available to the measuring device 2 is already provided in the probe 1. The measuring device 2 is used only as a signal recorder.

All of the illustrated features of the exemplary embodiments and the features of the claims can be combined arbitrarily with one another. In particular, different probes 1 with different channel outputs can be connected to different inputs 3 of a measuring device 1.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

What is claimed:

1. A system comprising a probe and a measuring device, wherein the probe is connected to an input of the measuring device, wherein an analog-digital converter is connected downstream of the input of the measuring device, wherein the probe provides a converter for the generation of a value-discrete and/or time-discrete signal from an analog input signal and wherein the value-discrete and/or time-discrete signal is supplied to the analog-digital converter of the measuring device, wherein the converter of the probe provides a higher resolution than the analog-digital converter of the measuring device.

2. The system according to claim 1, wherein the probe provides a first probe input and a second probe input, and wherein each of the probe inputs registers the same measurement parameter.

3. The system according to claim 1, wherein the probe provides a first probe input and a second probe input, and wherein each of the probe inputs registers different measurement parameters.

4. The system according to claim 1, wherein the probe provides at least one second converter for the generation of a second value-discrete and/or time-discrete signal from the analog input signal, and wherein the second value-discrete and/or time-discrete signal is supplied to a second analog-digital converter of the measuring device at a second input.

5. The system according to claim 1, wherein a value-continuous, time-discrete signal is supplied to the analog-digital converter of the measuring device.

6. The system according to claim 1, wherein a value-discrete, time-continuous signal is supplied to the analog-digital converter of the measuring device.

7. The system according to claim 1, wherein the supplied value-discrete and/or time-discrete signal forms a continuous datastream.

8. The system according to claim 1, wherein the supplied value-discrete and/or time-discrete signal comprises parameter information of the probe.

9. A method for registering an analog signal by using a system comprising a probe and a measuring device, the method comprising:
registering the analog signal by using the probe;
converting the registered analog signal into a value-discrete and/or time-discrete signal in the probe;
supplying the converted value-discrete and/or time-discrete signal to the measuring device; and
converting the value-discrete and/or time-discrete signal into a digital signal by the measuring device for further processing in the measuring device, wherein the converting the registered analog signal in the probe is performed at a higher resolution than the converting the value-discrete and/or time-discrete signal by the measuring device.

10. A system comprising:
a probe connected to an input of a measuring device, the probe including a converter to generate a value-discrete and/or time-discrete signal from an analog input signal, the probe to provide the value-discrete and/or time-discrete signal to the measuring device; and
the measuring device connected to the probe, the measuring device including an analog-digital converter that is connected downstream of the input of the measuring device, the converter of the probe providing a higher resolution than the analog-digital converter of the measuring device.

11. The system according to claim 10, wherein the probe includes a first probe input and a second probe input, and wherein each of the probe inputs registers the same measurement parameter.

12. The system according to claim 10, wherein the probe includes a first probe input and a second probe input, and wherein each of the probe inputs registers different measurement parameters.

13. The system according to claim 10, wherein the probe includes at least one second converter for the generation of a second value-discrete and/or time-discrete signal from the analog input signal, and wherein the second value-discrete and/or time-discrete signal is supplied to a second analog-digital converter of the measuring device at a second input.

14. The system according to claim 10, wherein the probe is configured to supply a value-continuous, time-discrete signal to the analog-digital converter of the measuring device.

15. The system according to claim 10, wherein the probe is configured to supply a value-discrete, time-continuous signal to the analog-digital converter of the measuring device.

16. The system according to claim 10, wherein the supplied value-discrete and/or time-discrete signal forms a continuous datastream.

17. The system according to claim 10, wherein the supplied value-discrete and/or time-discrete signal comprises parameter information of the probe.

* * * * *